United States Patent
Bradley

(10) Patent No.: US 10,380,327 B1
(45) Date of Patent: Aug. 13, 2019

(54) MEDICATION TRACKING AND NOTIFICATION DEVICE

(71) Applicant: Rachel E. Bradley, Leavenworth, KS (US)

(72) Inventor: Rachel E. Bradley, Leavenworth, KS (US)

(*) Notice: Subject to any disclaimer, the term of this patent is extended or adjusted under 35 U.S.C. 154(b) by 402 days.

(21) Appl. No.: 15/447,057

(22) Filed: Mar. 1, 2017

Related U.S. Application Data

(60) Provisional application No. 62/302,723, filed on Mar. 2, 2016.

(51) Int. Cl.
*G06F 19/00* (2018.01)
*G06F 3/147* (2006.01)
*G06Q 10/10* (2012.01)
*G08B 21/24* (2006.01)

(52) U.S. Cl.
CPC .......... *G06F 19/3456* (2013.01); *G06F 3/147* (2013.01); *G06Q 10/109* (2013.01); *G08B 21/24* (2013.01)

(58) Field of Classification Search
CPC ... G06F 19/3456; G06F 3/147; G06Q 10/109; G08B 21/24
USPC ...................................... 340/309.16
See application file for complete search history.

(56) References Cited

U.S. PATENT DOCUMENTS

| | | | |
|---|---|---|---|
| 4,293,845 A * | 10/1981 | Villa-Real | A61B 5/00 340/309.3 |
| 4,361,408 A | 11/1982 | Wirtschafter | |
| 4,419,016 A * | 12/1983 | Zoltan | A61J 7/0481 368/10 |
| 4,588,303 A | 5/1986 | Wirtschafter | |
| 4,731,051 A | 3/1988 | Fischell | |
| 4,849,948 A | 7/1989 | Davis | |
| 5,805,051 A * | 9/1998 | Herrmann | A61J 7/0481 221/2 |
| 6,084,504 A | 7/2000 | Rosche | |
| 6,314,384 B1 * | 11/2001 | Goetz | G06F 19/3456 702/177 |
| 7,944,342 B2 * | 5/2011 | Sekura | G06F 19/3456 340/309.4 |
| 8,149,096 B2 | 4/2012 | Metry | |
| 8,279,076 B2 | 10/2012 | Johnson | |
| 8,284,068 B2 | 10/2012 | Johnson | |
| 8,502,692 B2 | 8/2013 | Johnson | |
| 8,536,987 B2 | 9/2013 | Metry | |

(Continued)

*Primary Examiner* — Kerri L McNally
(74) *Attorney, Agent, or Firm* — DLA Piper LLP (US)

(57) ABSTRACT

A notification device that includes a housing, a processing unit in the housing, and a control panel and a visual display on the housing. The processing unit causes the display to visually display a dosage amount, receives a first medication taken command from the control panel, causes the display to visually display a time of day that the first medication taken command is received, receives a second medication taken command from the control panel, causes the display to visually replace the time of day that the first medication taken command is received with a time of day that the second medication taken command is received, causes the display to visually display a number of times that medication taken commands are received from the control panel within a specified time period, and causes the display to visually display a number of total medication taken within the specified time period.

14 Claims, 13 Drawing Sheets

(56) References Cited

U.S. PATENT DOCUMENTS

| | | | |
|---|---|---|---|
| 2006/0139150 A1* | 6/2006 | Brue | A61J 7/0481 340/309.16 |
| 2009/0222130 A1* | 9/2009 | Morse | A61J 7/0472 700/225 |
| 2010/0270257 A1* | 10/2010 | Wachman | G06Q 10/10 215/228 |
| 2014/0236617 A1* | 8/2014 | Oberfest | G06F 19/3456 705/2 |
| 2017/0098056 A1* | 4/2017 | Reddy | G06F 19/3456 |

* cited by examiner

MEDICATION TRACKING AND NOTIFICATION DEVICE

RELATED APPLICATIONS

This application claims the benefit of U.S. Provisional Application No. 62/302,723, filed Mar. 2, 2016, and which is incorporated herein by reference.

FIELD OF THE INVENTION

The present invention relates to containers for medication.

BACKGROUND OF THE INVENTION

Many medications are offered or prescribed on an "as needed basis," meaning the patient takes the medication only as needed for treatment (e.g. to alleviate pain). These types of medications usually have safe limits in terms of the amount of the medication per dose, the proximity of consecutive doses, and total amount or number of doses that can be safely taken in any given 24 hour period.

Prior art devices exist for tracking medication consumption, which typically provide an alert when it is safe to take the next dosage. For example, if a pain medication can only be taken once every four hours, then an audible or visual alert is provided when the four hours is up and the next dosage can be taken. However, there are several drawbacks to such devices. First, the alert serves to remind the user to take the next dose even if the user is not quite ready for the next dose. When consuming "as needed" medications, it is best to only take the medication when really needed, not when commanded or suggested that the next dose can safely be taken by a tracking device. Second, many times if doses are taken every time the minimum dosage proximity time is reached, then the safe number of dosages that can be taken in any given 24 hour period is often exceeded. For example, popular pain medications can be taken once every four hours, but no more than four times in one 24 hour period. A 4 hour proximity time period alone would call for 6 doses per 24 hours. Conventional reminder devices don't track the number of doses over each 24 hour period. This problem is made worse if the amount of each dose is varied. Therefore, conventional medication dose reminder devices are inappropriate and deficient for "as needed" medications because they tend to induce the user to take more medication, more often, than would otherwise be needed.

BRIEF SUMMARY OF THE INVENTION

The aforementioned problems and needs are addressed by a notification device that includes a housing, a processing unit disposed in the housing, the processing unit including a clock and a processor, a control panel on the housing and communicatively coupled to the processing unit, and a visual display on the housing and communicatively coupled to the processing unit. The processing unit is configured to cause the display to visually display a dosage amount, receive a first medication taken command from the control panel, cause the display to visually display a time of day that the first medication taken command is received, receive a second medication taken command from the control panel, cause the display to visually replace the time of day that the first medication taken command is received with a time of day that the second medication taken command is received, cause the display to visually display a number of times that medication taken commands are received from the control panel within a specified time period, and cause the display to visually display a number of total medication taken within the specified time period, wherein the number of total medication taken is equal to the displayed dosage amount multiplied by the number of times that medication taken commands are received from the control panel with in the specified time period.

Other objects and features of the present invention will become apparent by a review of the specification, claims and appended figures.

DETAILED DESCRIPTION OF THE INVENTION

The present invention is a battery operated medication tracking and notification device that tracks medication intake and indicates when it is safe for the next dose taking into account minimum times between doses and maximum doses per 24 hour time periods, even when the amount of each dose is varied. The device does not alert the user the moment the next dosage is safe to take, but rather provides this information to the user when the user deems the next dosage may be "needed" and looks at the display of the device. The device is especially advantageous over manual efforts to track medication intake given the user is usually not in a condition to track and calculate dosages and dose times (e.g. by writing times and dosages down). The device attaches to the container holding the medication, to minimize confusion over other medications and to maximize user input accuracy (i.e., remind the user to input dosage intake at the moment of medication consumption). For users taking multiple different "as needed" medications, having one tracking and notification device for each medication safely, accurately and independently tracks intake of each medication (no matter how different intake schedules are).

Figure 1:
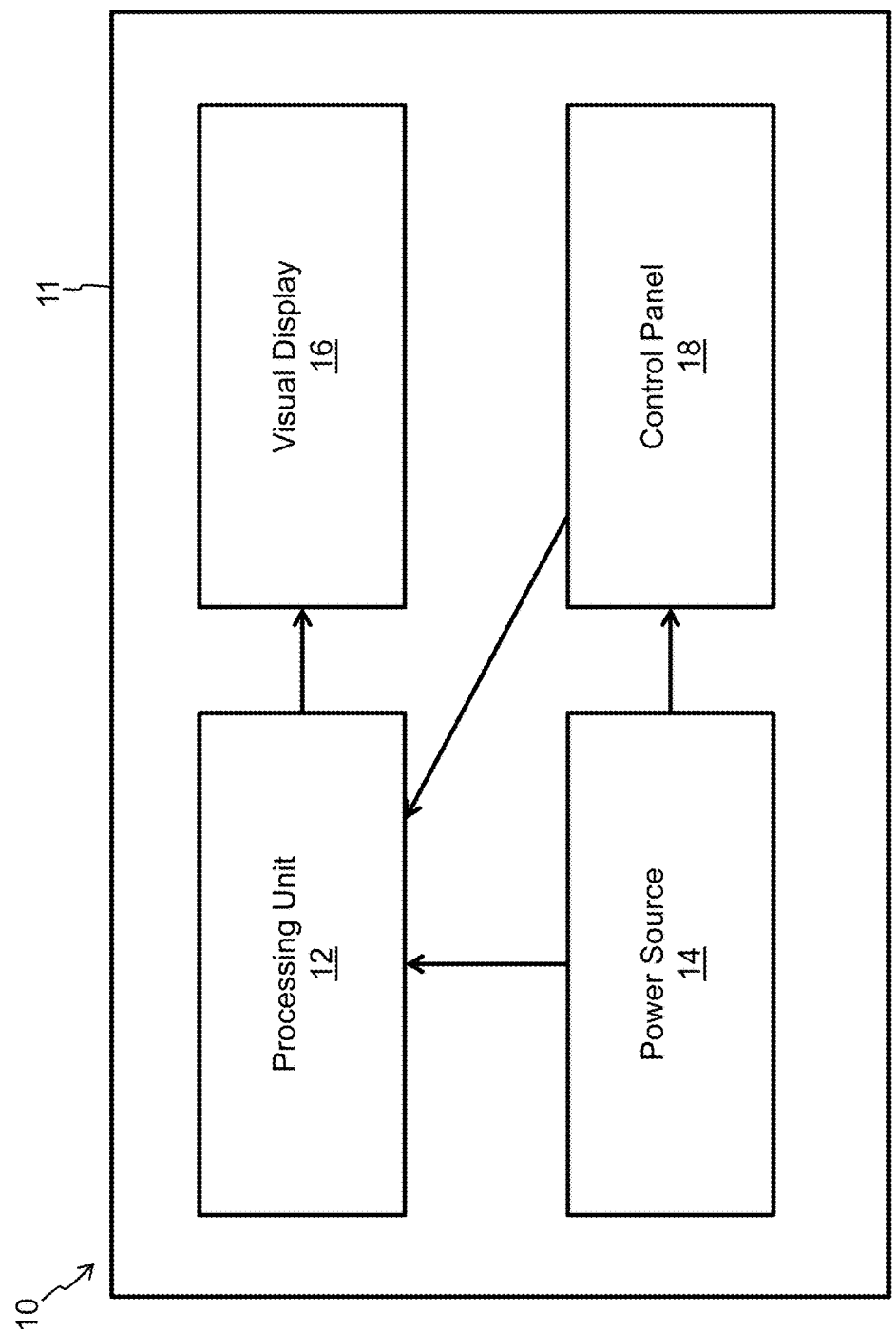
FIG. 1 is a schematic view of the medication tracking and notification device.

The major components of the medication tracking and notification device 10 are schematically shown in FIG. 1. Device 10 includes a housing 11 which contains therein a processing unit 12, and a power source 14 such a battery for supplying power to the processing unit and other device components. The processing unit 12 includes an internal clock, a processor for receiving and processing commands and data, and an internal memory (volatile and/or non-volatile) for storing operational parameters and commands. The front of the housing includes a visual display 16 and a control panel 18 with buttons or switches for operating the device 10. Processing unit 12 controls the operation of the device 10, using the power source 14 to keep its internal clock and calendar running, and keep the time and dosage information visible on the visual display 16. Preferably, the device 10 includes a tab that when removed connects the power source 14 to the processing unit 12 for the first time (i.e., so that batter power is not consumed until after purchase and shortly before first use).

Figure 2:
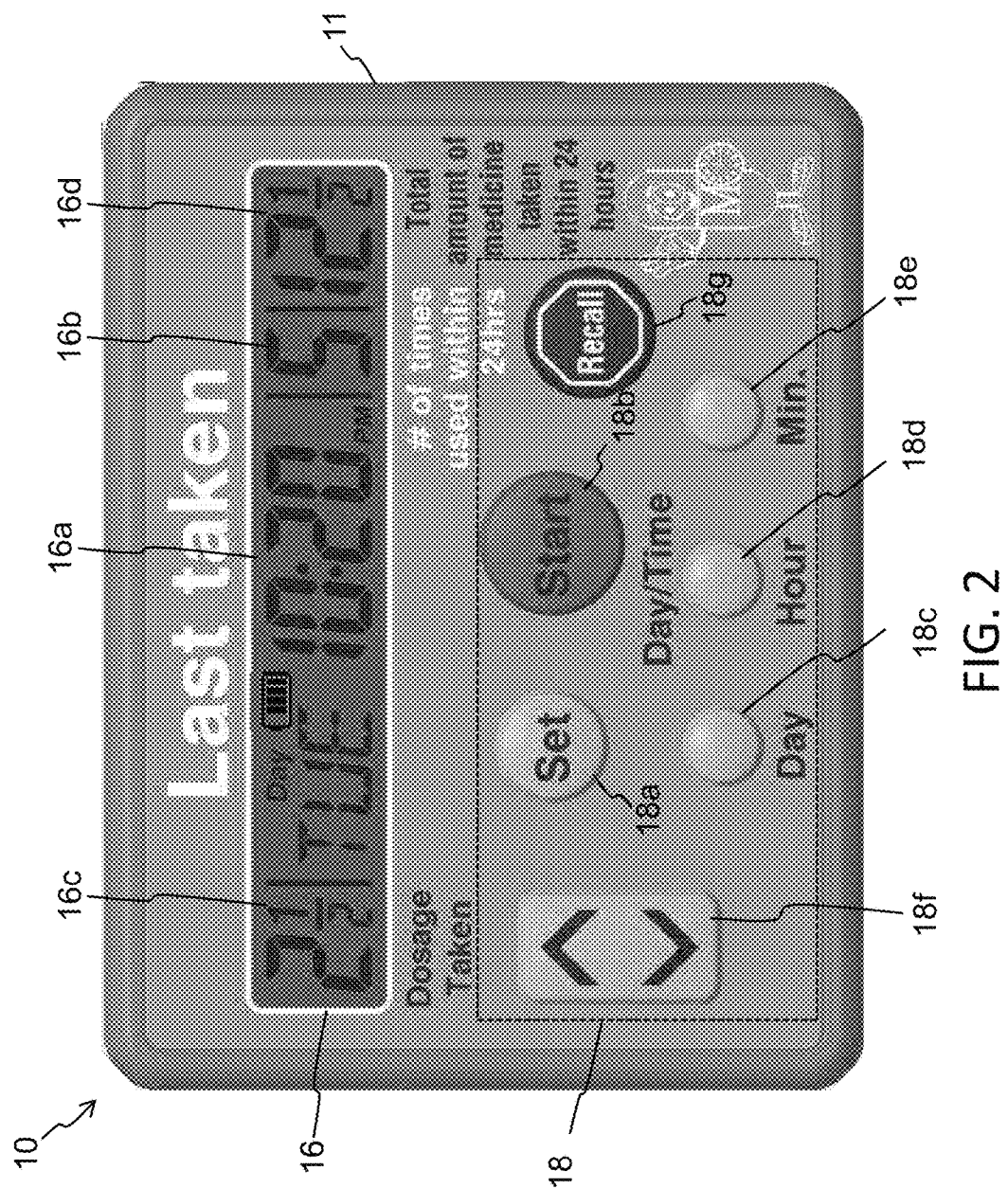
FIG. 2 is a view of the front panel of the medication tracking and notification device.

FIG. 2 illustrates the front panel of the device 10 containing the visual display 16 and the control panel 18. The visual display 16 can include a single image panel, or multiple such panels. For example, as shown in FIG. 2, the visual display 16 includes a first image panel 16a (displaying the time and day, and displaying a battery icon that changes in appearance to indicate the present level of charge on the internal battery so that a user can replace the battery before it becomes depleted), a second image panel 16b (displaying the number of times within the last 24 hours that medicine has been consumed), a third image panel 16c (displaying the dosage to be taken together at any single time), and a fourth image panel 16d (displaying the total dosages taken in the last 24 hours). The control panel 18 includes a plurality of buttons and/or switches. For example, as shown in FIG. 2, the control panel 18 includes a set button 18a, a start button 18b, a day button 18c, an hour button 18d, a minute button 18e, scroll arrow buttons 18f, and a recall button 18g.

When the device 10 is first started (i.e., the tab is pulled and processing unit is powered up for the first time), dashes will appear across the visual display 16 indicating that the date and time need to be set. When the user pushes the "Set" button 18a, that will cause the visual display to indicate 1/1/17 as a default starting date. To change this, the user holds the set button 18a, while also pressing the hour button 18d to change the month (it will 'flash' as the number changes). While still holding the set button 18a, the user pushes the day button 18c to change the day, which will then flash. Then, while still holding the set button 18a, the user pushes the arrows 18f to change the year, which is then flashing. After releasing everything, within one minute, daylight savings time can be changed to 'off', for those areas not affected by it. Otherwise, it is automatically 'on'. This is done by the user holding the set button 18a and the minute button 18e to change between Yes or No (which are now flashing), indicating if the user's area honors daylight savings time or not. Release all the buttons and then press the set button again, after which the visual display will display "1 Sunday, 12:00 am 1" as a 'starting' position to set the timer. Lastly, to set the time, the user can press and hold the set button 18a within one minute of the previous display, and at the same time the day button 18c to set the day, the hour button 18d to set the hour, and the minute button 18e to set the minutes. If anything was done incorrectly, all buttons can be released and started again (e.g., when the set button 18a is hit again and the date schedule appears again to start the entire process over). Once the time is entered, the user can release the set button 18a and within one minute, choose a desired dosage using the arrow buttons 18f, so when the device is actually used for the first time, the dosage will begin at a number that is likely for that medication. If the default dosage is not correct, it can be changed by using the up and down arrows 18f to the preferred amount. The device always returns to the last 'dose amount' taken. These settings will remain secure and will not change by accident if the device is ever bumped, since two buttons have to be held at the same time. If only set is pushed, and nothing else within a minute, then the previous values will return.

The user begins using the device by pressing the start button 18b, which will record the present time as one at which medication was taken. The user has 60 seconds to change the dosage using the up/down arrows 18f to reflect the dosage amount taken at this time. The default is the dosage for the last time the medication was taken. The dosage can be adjusted from ½, to 1, to ½, etc., up to 9%, and then back to ½. By having the dosage represented in ½ increments, liquid measurements as well as partial pills can be accommodated. Using the up and down arrows 18f will allow the dosage to be changed easily. If the user always uses the same dose of a particular medicine, then only the start button 18b will ever need to be pressed. After 60 seconds of inactivity, the dosage and time taken are recorded. The visual display will continue to display the time of day and dosage for the last time the medication was taken, along with the current number of times and total dosage taken in the last 24 hours. At any given time, visual panel 16b indicates how many times medication has been taken within the last 24 hours, and visual panel 16d indicates the total number of dosages that have been taken within the last 24 hours. For example, if a double dose is initially taken, and 12 hours later another single dose is taken, then afterward the visual panel 16a would indicate the time of the second taking of the medication, the dosage panel 16c would indicate the number 1 (indicating the dosage for the second taking of the medication), the visual panel 16b would indicate the number 2 to indicate that the medication was taken twice in the last 24 hours, and the visual panel 16d would indicate the number 3 to indicate that a total of 3 dosages was taken over the last 24 hours.

If the unit is not used for a full 24 hour period, then the unit will go into a sleep mode, where dashes appear in the visual display 16 to indicate the unit is operational but not currently in use. If a button other than the start button 18b is pressed after the one minute interval, then the device will assume this is an inadvertent bump and will stay in its current state. If the start button 18b is pressed more than once within the same one minute timeframe, then the number of times used visual panel 16b will not be incremented again.

The recall button 18g allows the user to view previous times that medicine was taken. If the recall button 18g is pressed during the 60 second setting window where the dose can be set, the display will show the previous time that medicine was taken. Repeatedly pressing the recall button will scroll back to show previous times medication was taken, going back to the last the sleep mode. Once finished looking at the previous times, the display will automatically go back the very last setting. If after viewing previous times that medication was taken, the user still wants to take medicine, then they can press the start button 18b again. If not, then they can wait until a better time. This way the user can look back at all the doses taken since the last 'sleep mode' to know when they started the current doses, and confirm if they really want to take the medication at this time. Therefore, hitting the start button 18b and then the recall button 18g without again hitting the start button 18 will cancel the current start so the device knows no new medicine was just taken.

Figure 3:
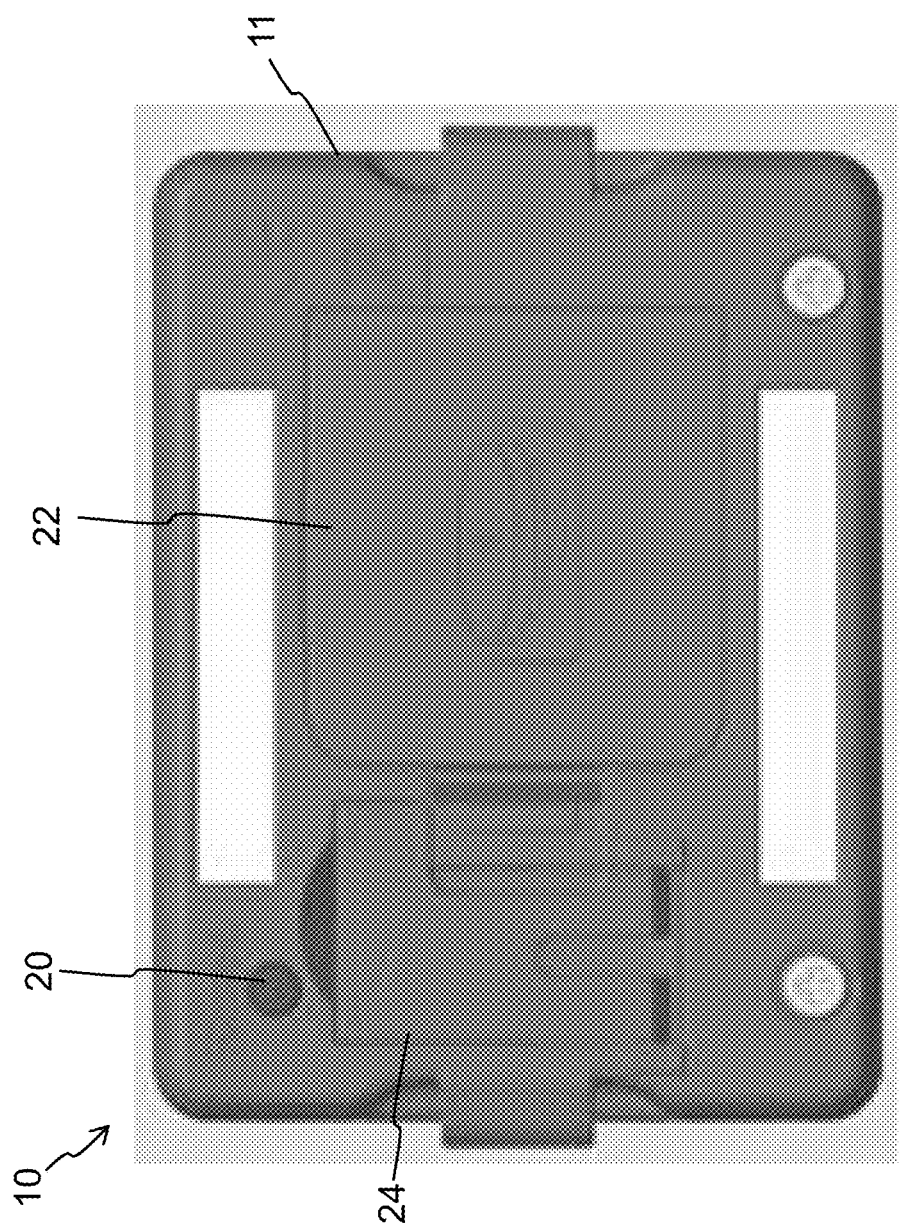
FIG. 3 is a view of the back panel of the medication tracking and notification device.

FIG. 3 illustrates the back panel of the housing 11. The back panel can include a reset button 20 to restart the unit including resetting the clock as well as the number of times used and number of dosages in the last 24 hours. A battery compartment 22 secures the battery and includes a cover that can be removed to change the battery. A foldable stand 24 can rotatably extend from the back panel to prop up the device.

Figure 4A:
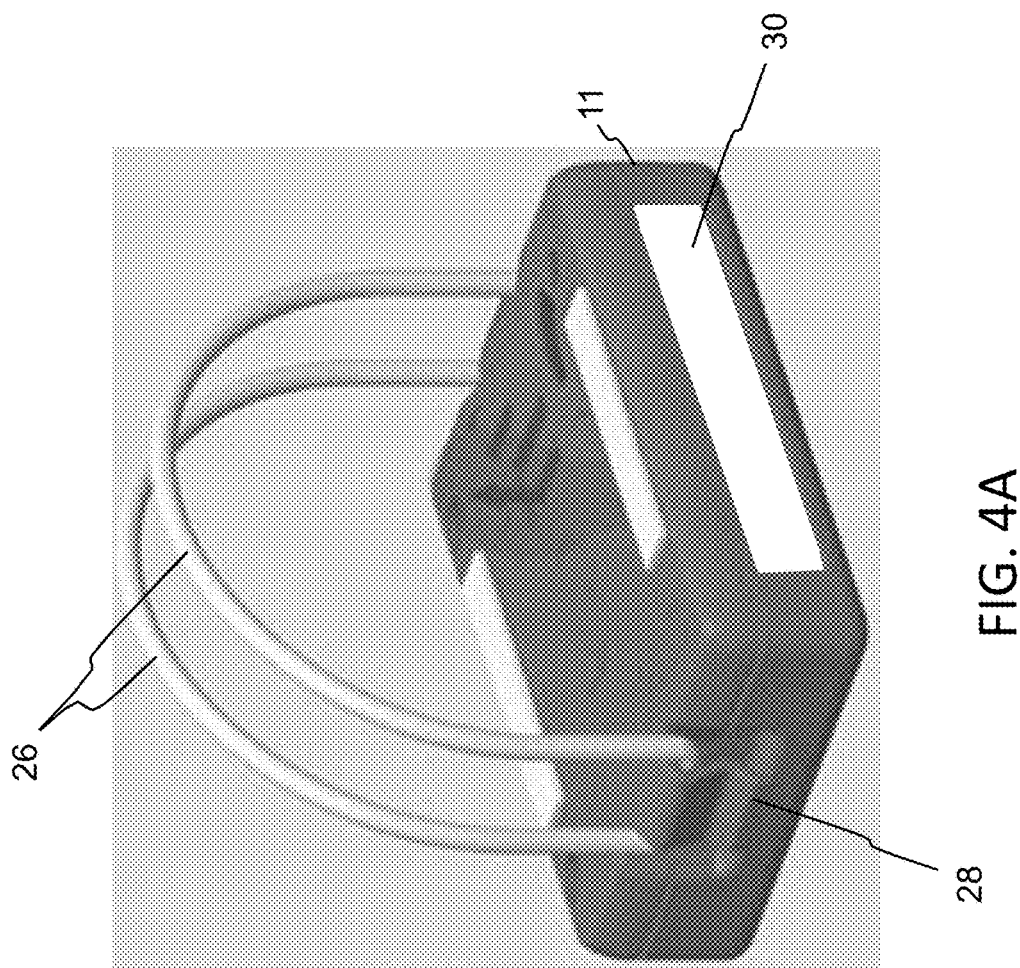
FIG. 4A is a perspective view of the back of the medication tracking and notification device.
Figure 4B:
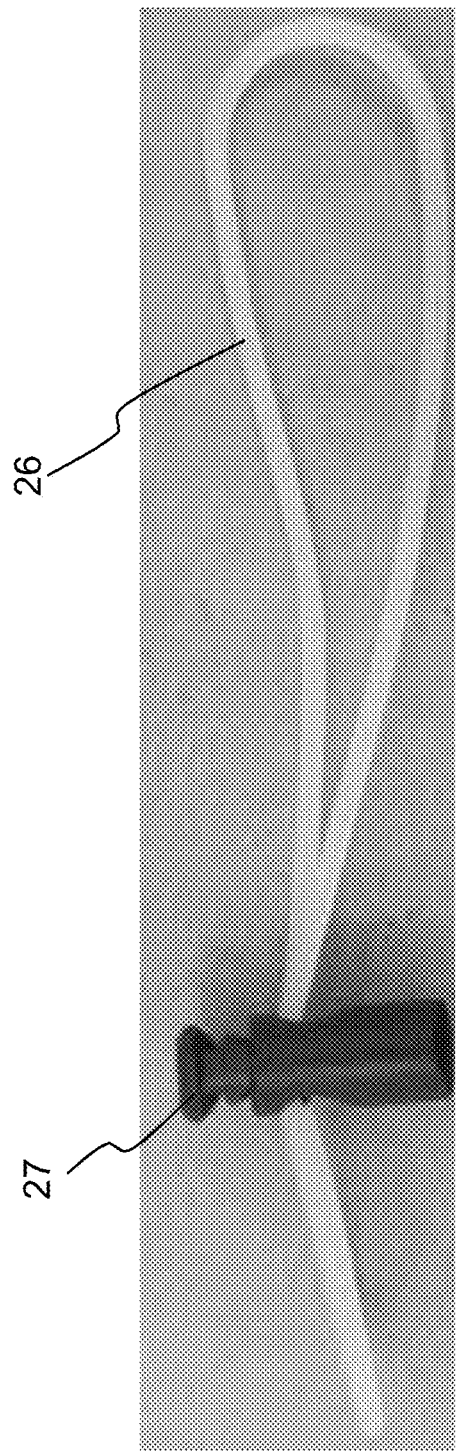
FIG. 4B is a top view of a strap for the medication tracking and notification device.

One or more straps 26 extend from the housing 11 to secure it to the medication container, as shown in FIG. 4A. Straps 26 removably engage with a tab 28 on the side of device 10, and are preferably made of rubber or other elastic material so that straps 26 can be stretched around and engage with containers of different sizes and shapes. A single round strap has the advantage of being easily rolled up or down if there was a need to read any covered portion of the medication container. Straps of clear material allow the user to read through the straps. Alternately, the one or more straps 26 could be made of hook and fabric material to easily and releasably engage with medication containers. Other strap configurations include snaps, belt & buckle, cinch cord, etc. For example, FIG. 4B shows a strap 26 with a spring loaded fastener 27 for easily securing the strap to a medication container (not shown).

One or more sides of housing 11 can include a special coating or other material 30 conducive for writing, such as a name of a user or special instructions or identification of either the user or the medication, as shown in FIG. 4A. This can help prevent confusion if more than one person in the household are using devices 10 for their medication. The housing can also be provided in different colors and/or materials, and/or shapes, to make them distinguishable for different users and/or different medications.

Figure 5A:
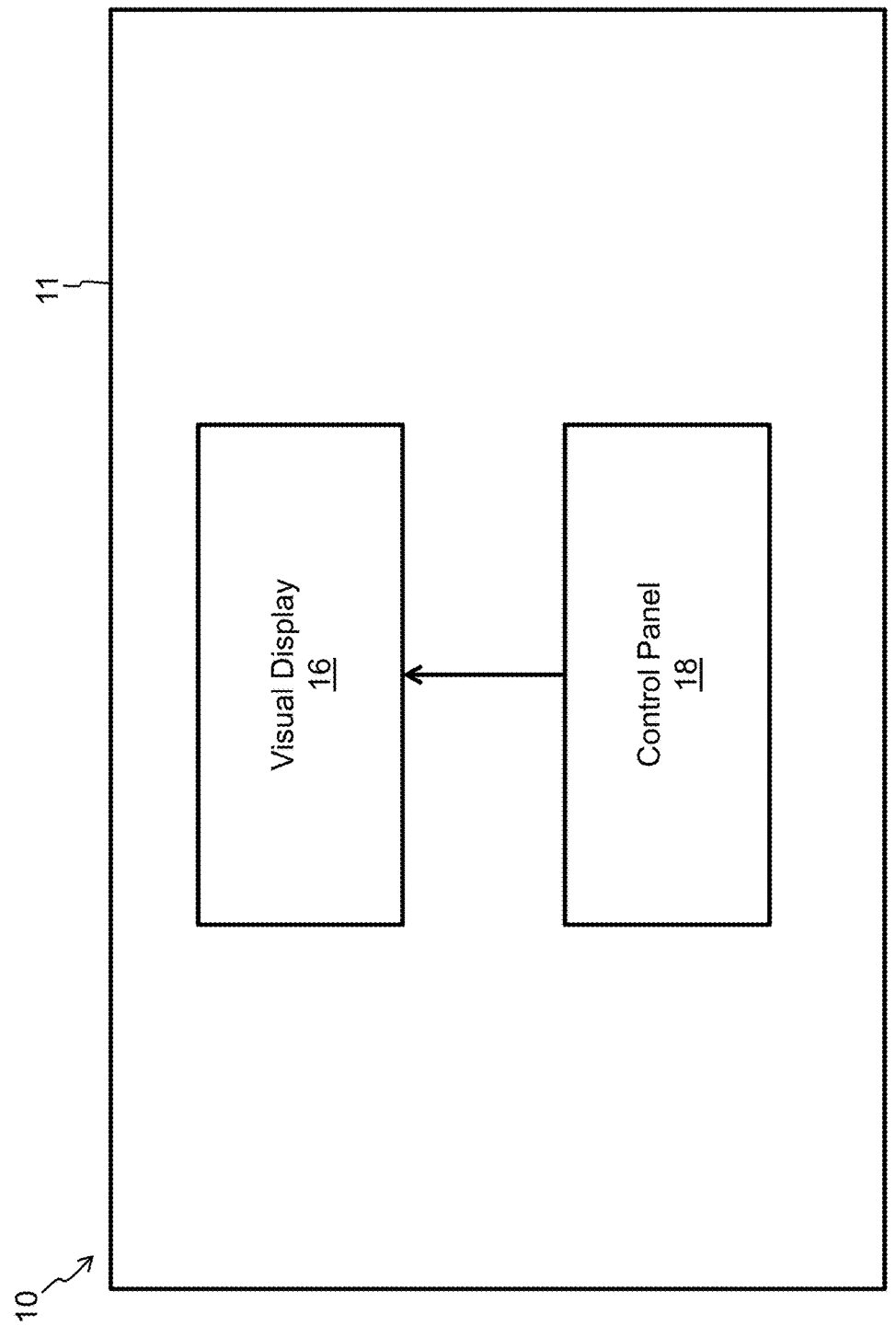
FIG. 5A is a schematic view of an alternate embodiment of the medication tracking and notification device.
Figure 5B:
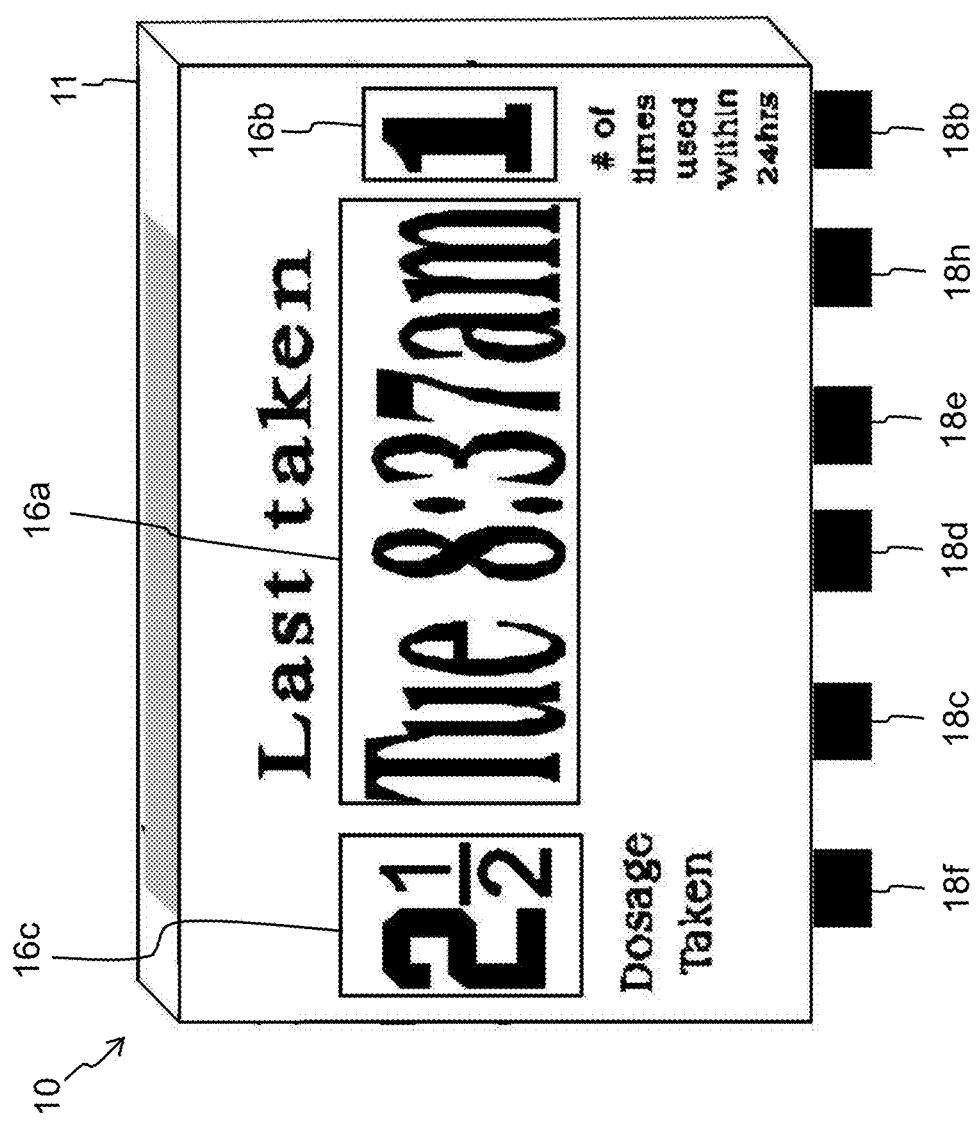
FIG. 5B is a front view of the alternate embodiment of FIG. 5A.

FIG. 5A schematically illustrates an alternate embodiment, where the processing unit and power supply are omitted. FIG. 5B illustrates the front panel of this embodiment. Instead, the visual display 16 includes rotating wheels with indicia, which are mechanically operated by mechanical control panel buttons. For example, the dosage counter 16c is still incremented with each activation of the dosage taken button 18f from ½ to 1 to ½, etc. up to 9½ and then starts over at ½. The day of display 16a will increment with each activation of the day button 18c, from Sun., to Mon to Tue, etc. and will start over after Sat. The time of display 16a is set by incrementing hours using the hour button 18d, and by incrementing minutes using the minute button 18e. An additional button 18h can be added to increment AM to PM, and vice versa. The number of times taken 16b is incremented by activating the start button 18b. The main advantage of this mechanical embodiment is that no batteries are ever required or need to be replaced.

Figure 6:
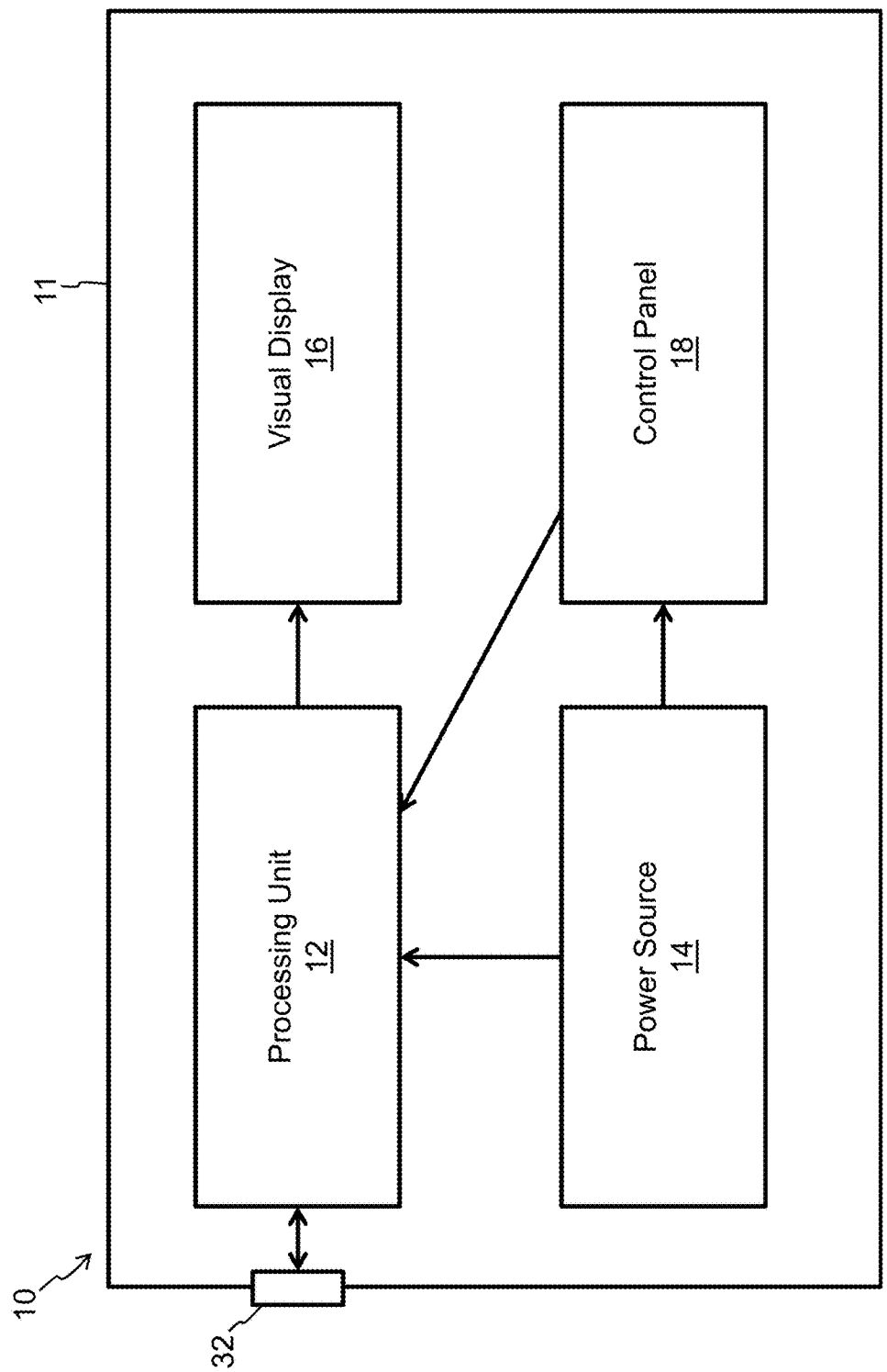
FIG. 6 is a schematic view of a second alternate embodiment of the medication tracking and notification device.

FIG. 6 illustrates another embodiment, where the processing unit 12 includes an internal memory that records all the parameters input by the user, including when the user took the various dosages of the medication and in what amounts. The device 10 includes a port 32 for exporting the stored information to an external network or computer. For example, port 32 can be a USB port for connecting the device 10 to a network or computer. Port 32 could be a memory card reader, for exporting the data onto a memory card inserted into the port 32, which can be removed and read by a computer. Port 32 could be a wireless transceiver (Wi-Fi, Bluetooth, etc.), which can wirelessly export the data to a wireless network. Port 32 could allow remote monitoring of medication consumption by, for example, the prescribing doctor or issuing pharmacy, who will receive dosage information real time or in periodic updates sent over a network. Refills could automatically be triggered by providing medicine consumption information to the prescribing doctor and/or issuing pharmacy which is based on actual medication consumption by the user, as opposed to mere time period which would be a less accurate method of refilling medication.

The device 10 can be configured to draw low power during times of non-use. The visual display 16 can be configured to turn on for a specified time only when any of the buttons are activated, and remain off during long periods of non-use. The processing unit 12 could include a motion sensor or accelerometer, so that any movement near the device 10, or any movement of the device 10, would turn on the display 16, including a backlight of display 16, that would make it easier to find in a dark room. The housing 11 can be made of a light absorbing material that glows in the dark, making it easier to find in the dark.

Figures 7A, 7B:
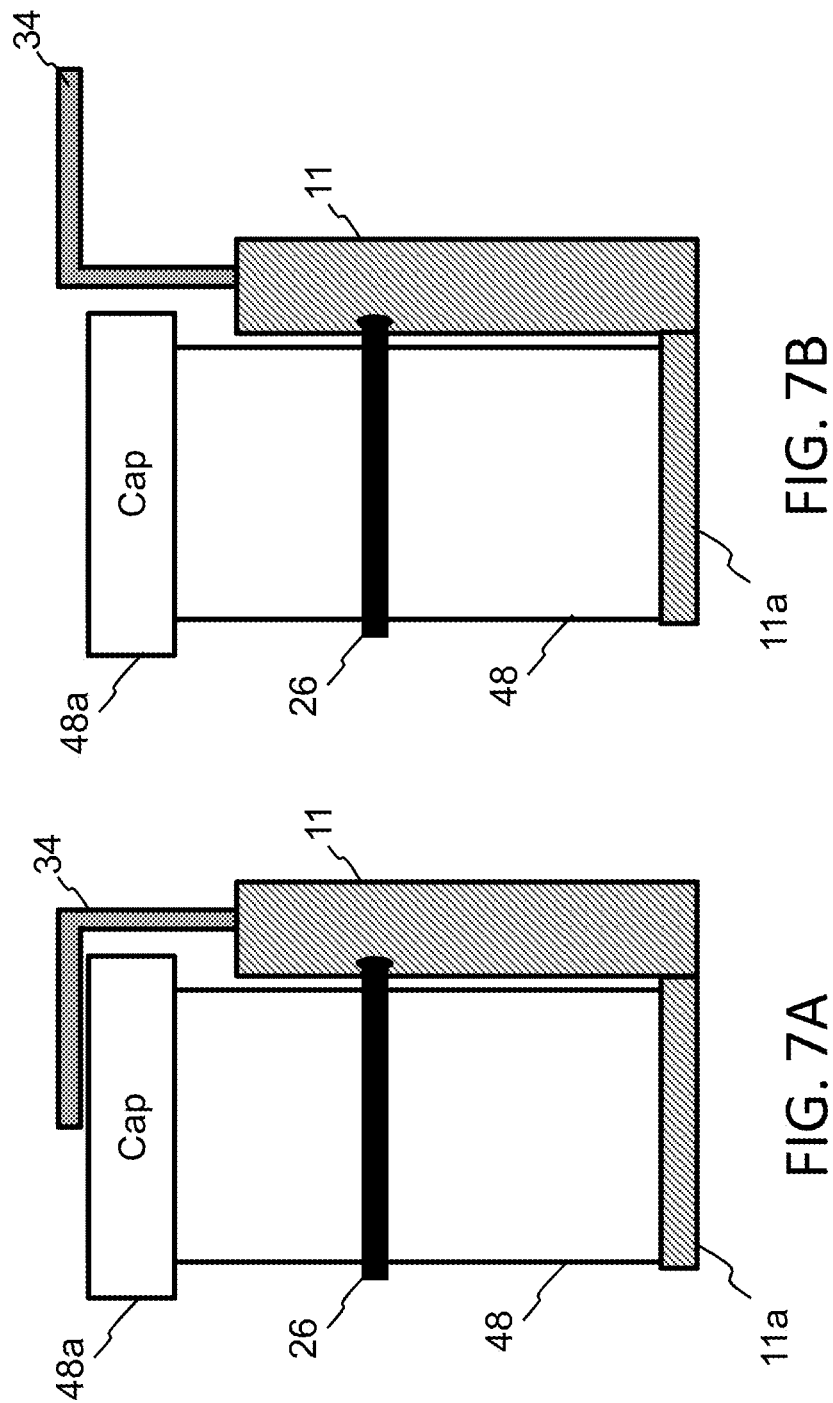
FIG. 7A is a side view of the medication tracking and notification device with the locking arm in the locked position.
FIG. 7B is a side view of the medication tracking and notification device with the locking arm in the unlocked position.
Figure 7C:
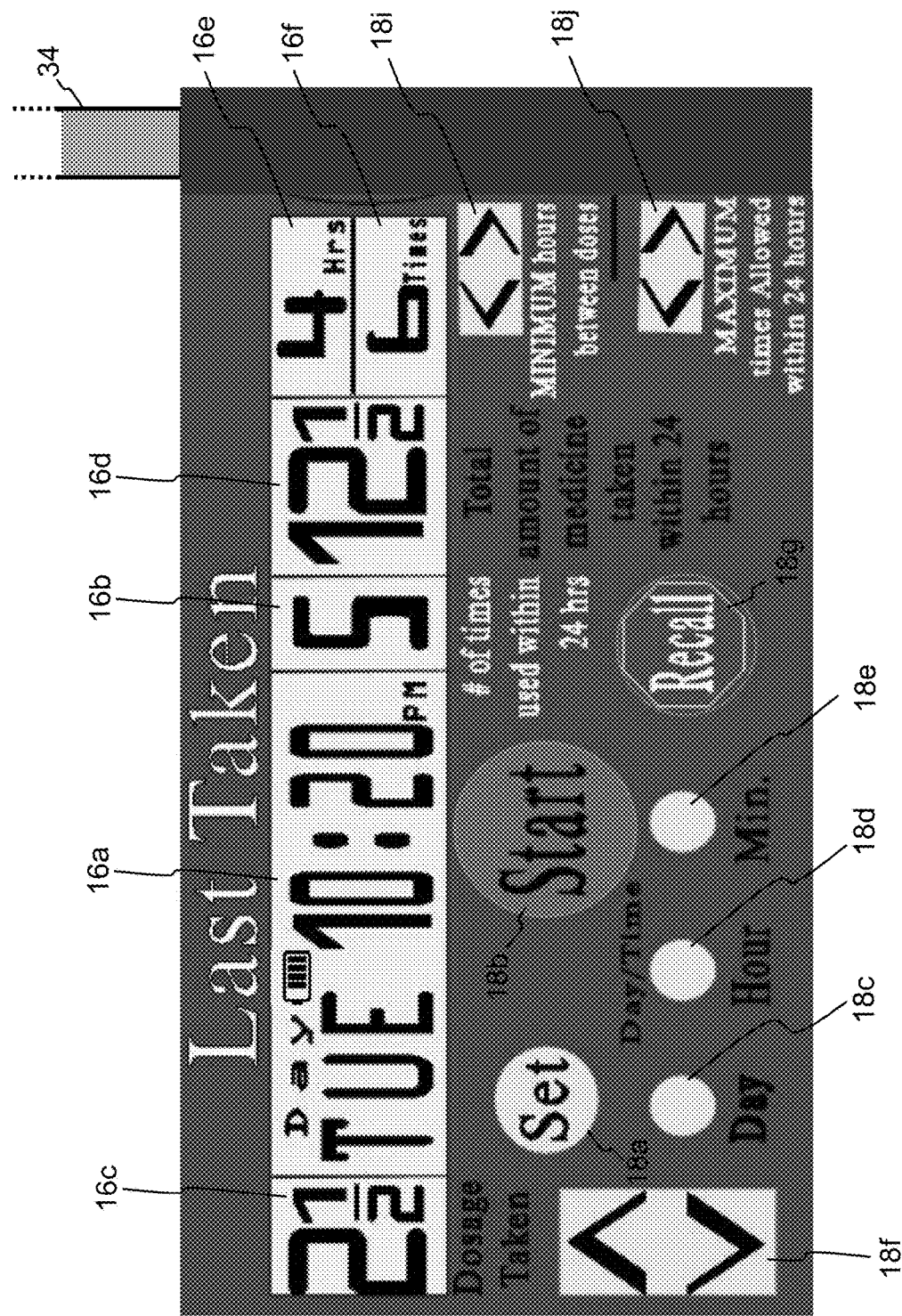
FIG. 7C is a view of an alternate embodiment of the front panel of the medication tracking and notification device.

Device 10 can include a locking arm 34 that engages with the lid 48a of the medicine container 48, as shown in FIGS. 7A and 7B. The locking arm 34 can rotate between a locked position that is positioned over the lid 48a of the container 48 as shown in FIG. 7A (which prevents access to the medicine in the container by preventing the lid from being opened), and an unlocked position that is positioned away from the lid of the container as shown in FIG. 7B (which allows access to the medicine in the container). The locking arm 34 is configured to be rotatable to the unlocked position only if the time since the last dosage is greater than a predetermined time amount, or the total number of dosages in the last 24 hours is under a predetermined number, such that it is safe to take the next dosage of the medication. The housing 11 preferably includes a base 11a extending from the back panel on which the medication container sits. As shown in FIG. 7C, the user can program the device 10 with the safe dosage time intervals as shown in image panel 16e using buttons 18i, and with the total 24 hour maximum dosages that are indicated for the medication at issue as shown in image panel 16f using buttons 18j, and the processing unit 12 would operate the locking arm accordingly to give the user extra incentive to wait until the next dosage can be taken. The locking arm 34 can include a gear, tab or other mechanical element that engages with another mechanical element operated by the processing unit to allow or prevent movement of the locking arm.

Figure 8A:
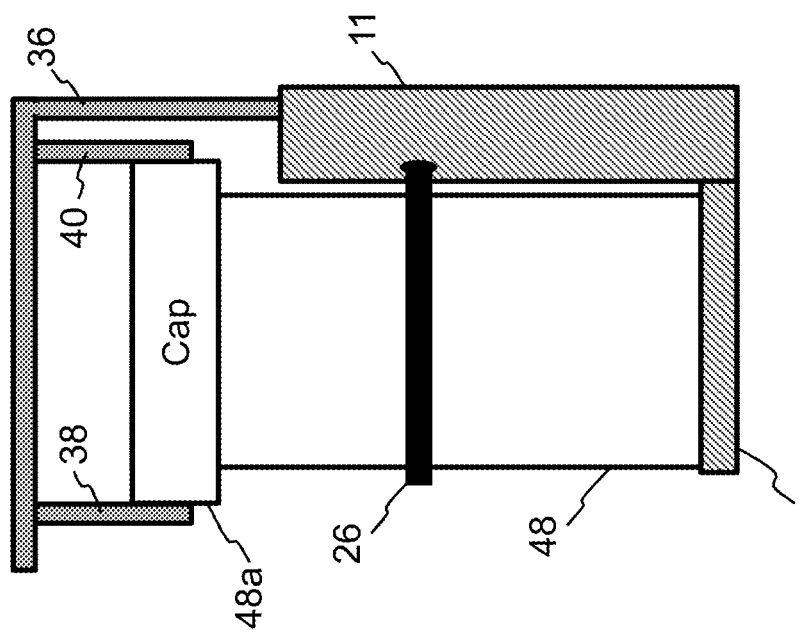
FIG. 8A is a side view of an alternate embodiment of the medication tracking and notification device with the locking arm in the locked position.
Figure 8B:
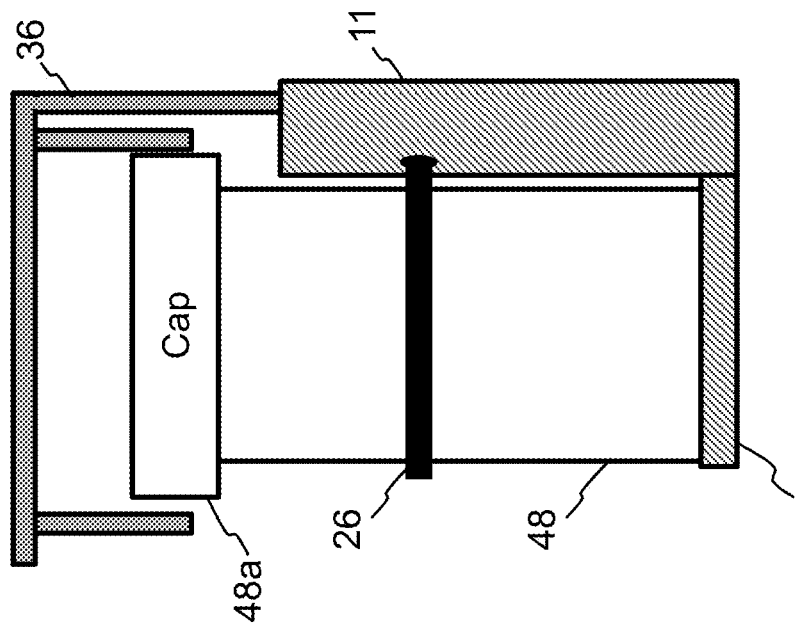
FIG. 8B is a side view of the alternate embodiment the medication tracking and notification device with the locking arm in the unlocked position.
Figure 8C:
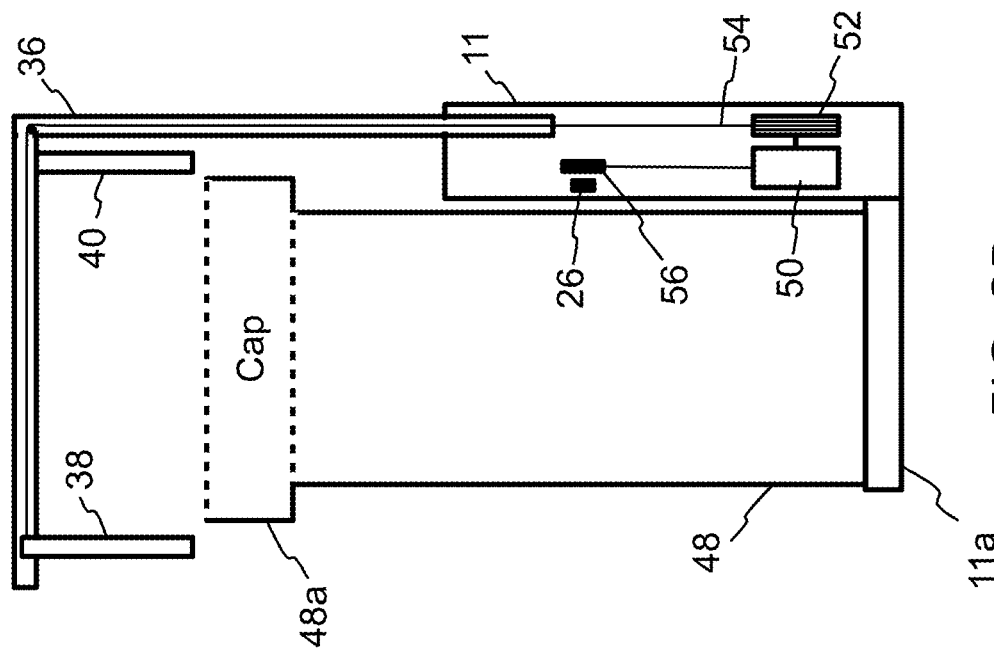
FIG. 8C is a side cross sectional view of the alternate embodiment of the medication tracking and notification device with the locking arm in the locked position.
Figure 8D:
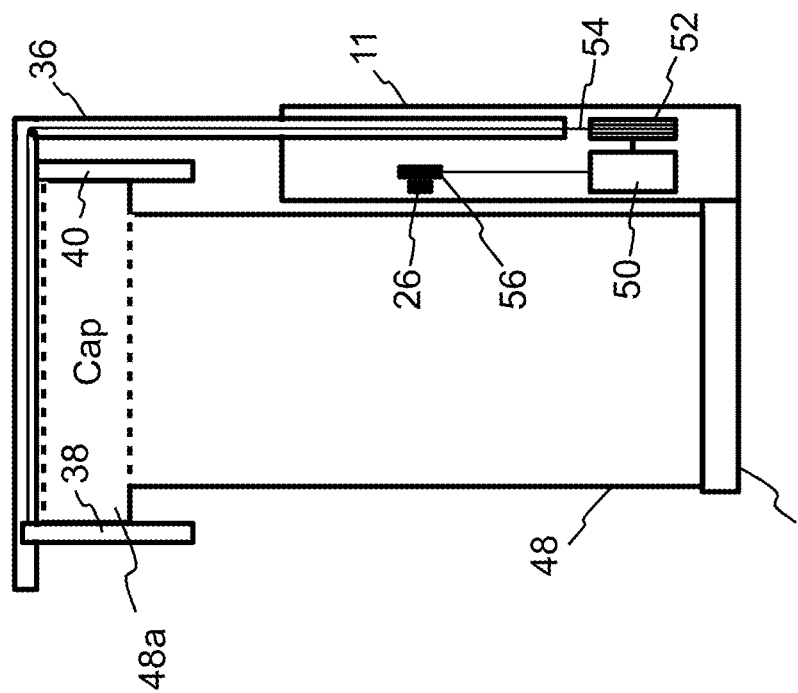
FIG. 8D is a side cross sectional view of the alternate embodiment the medication tracking and notification device with the locking arm in the unlocked position.

FIGS. 8A-8D illustrate another embodiment of a locking arm 36 which blocks access to the medicine container until the minimum time has lapsed and/or maximum dosage not exceeded, which includes downwardly extending arms 38 and 40 that retract to a locking position (FIG. 8A) that pinch the sides of the cap 48a to prevent it from being rotated and removed, and expand to a unlocking position (FIG. 8B) that are spaced away from the cap 48a so that it can be rotated and removed. The locking arm 36 in this embodiment can include gears, cables or other mechanical elements that move, or prevent the movement of, arms 38/40 under the control of the processing unit 12. A non-limiting example is illustrated in FIGS. 8C-8D. A motor 50 operated by processing unit 12 rotates a spool 52 that pulls on a cable 54, which in turn pulls on arm 38 to slide it into its locking position, as shown in FIG. 8C. Preferably locking arm 36 is slidable relative housing 11, so that the tightening of cable 54 caused the locking arm 36 to slide down so that arms 38 and 40 fulling engage with cap 48a. The motor 50 also operates a plate 56 which is pressed against the strap 26 to prevent it from sliding or moving (to prevent the medical container from being removed from the device 10). To unlock the device 10, cable 54 is released so that the arm 38 can be pulled away from cap 48a, arm 36 can be extended up, and plate 56 moved away from strap 26, as shown in FIG. 8D. In this unlocked position, the cap 48a can be removed from container 48, and if desired container 48 can be removed from device 10. Having arm 36 slidable relative to housing 11 allows the device 10 to accommodate containers 48 of different heights, and having arm 38 slidable relative to locking arm 36 allows for device 10 to accommodate container caps 48a of different widths. In both cases, pulling on cable 54 pulls locking arm 36 down and pulls arm 38 laterally in a single operation of motor 50.

Figure 9A:
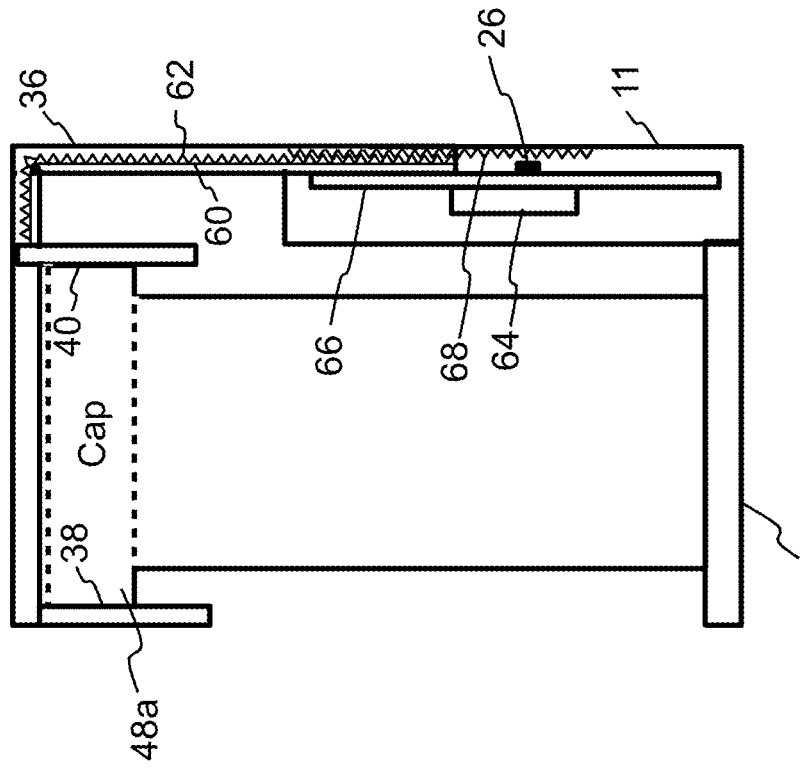
FIG. 9A is a side cross sectional view of another alternate embodiment of the medication tracking and notification device with the locking arm in the unlocked position.
Figure 9B:
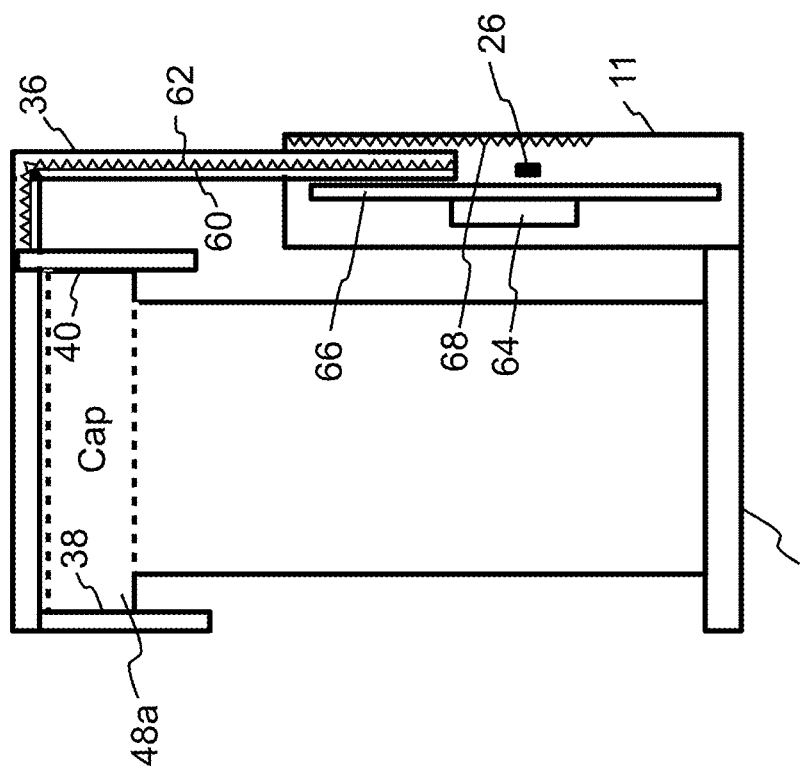
FIG. 9B is a side cross sectional view of the embodiment of FIG. 9A where the locking arm is in the locked position.

FIGS. 9A-9B illustrate another embodiment of the locking arm 36 which blocks access to the medicine container until the minimum time has lapsed and/or maximum dosage not exceeded, where arm 38 is fixed, but arm 40 slides under the control of a rigid cable 60 with teeth 62 on one side. Once the locking arm 36 is vertically positioned, and the arm 40 is horizontally positioned to engage with cap 48a, a motorized piston 64 drives a plate 66 that presses on locking arm 36 or cable 60 so that teeth 62 on rigid cable 60 engage with teeth 68 on the inside of housing 11, as shown in FIG. 9B. Once the teeth engage, the arms 36 and 40 are locked in position (i.e., arm 36 cannot move vertically, and arm 40 cannot move laterally). Plate 66 also presses against strap 26, preventing it from moving as well.

The locking mechanism is useful to discourage the user from accessing the medication before they should by providing a physical barrier to opening the medication container. While it is apparent that a true addict could break into the container despite the locking feature of device 10, the real advantage of the locking mechanism is to visually alert the user that they would have to break into the container locked by device 10, and doing so crosses a line to addiction that should not be crossed. Without the visual reminders provided by the display 16 and/or locking arm 36, which indicates the user shouldn't take more medication at that time, users tend to take too much medication and very quickly become addicted, which then leads to stronger drugs, more addictions, a total loss of health, and possibly even death. Device 10 is designed to provide sufficient incentive to avoid over-medication and addiction, and therefore the emotional hardship, economic loss, work productivity impact, and every other societal implication of addiction.

The device 10 has many advantages. It is specifically ideal for users who are using medications on an as needed basis. It does not activate any alarm or visual display to remind a user that it is time to take the medication. Specifically, the display never provides any specific visual indication, sound, flag, or other notice that the next dosage can be taken. Rather, the device provides a way of recording the user's medication input, and provides that information to the user when the user approaches and looks at the medication container because the user may need or want the medication. It provides a safe and reliable way for the user to confirm when the last dosage was taken and how many dosages have been taken in the last 24 hours, so that the user can know whether or not it is safe to take additional medication based on past dosages. The recall feature allows users to view all the dosages taken, up to when the device was last in 'sleep mode'. This way, any user that needs to take medication for days at a time can see when and how much medication was taken, so they know if they are getting too close to any maximum limitations.

The device 10 can include a clear cover ('shield') over the front of the device, that can flip up to provide access to the buttons, and flip down to cover the front of the device. The cover in the closed position will prevent any inadvertent activation of the buttons, allowing the user to store the device in a purse or backpack without fear of the buttons being bumped and activated when medicine was really not taken. For vision impaired users, the device can include Braille on the buttons. The device can also include a speaker and an audible output button on the side. When the button is depressed, and held, what is being displayed on the screen (e.g. "Dosage taken, 2½" "Time, Tuesday 10:20 am", etc.) will be output (spoken) by the speaker.

Device 10 encourages users to take medication only as needed, by simply giving all the information a user needs to make sure there is plenty of time between doses, and that they take no more than is allowed in a 24 hour period. Since many medications, especially pain medicines, are best used by taking the least amount needed to relieve pain, device 10 encourages users to take another dose only when the pain or other symptoms return. If the user is not in pain or suffering the symptoms addressed by the medication, the device does not provide any audible or visual alarm to which the body may react by enhancing or triggering symptoms. Prior art devices remind users when they can take the next dose. Device 10 specifically does not provide such a reminder. Rather, device 10 is backward looking should the user decide another dosage is desirable. By focusing on how much medication has already been taken, device 10 encourages users to walk away until their bodies say they need more. If they do need more then they will know, with confidence, it is okay to take another dose, or they will know it is too soon and they need to wait a little longer, depending on the information provided by device 10.

It is to be understood that the present invention is not limited to the embodiment(s) described above and illustrated herein, but encompasses any and all variations falling within the scope of any claims. For example, references to the present invention herein are not intended to limit the scope of any claim or claim term, but instead merely make reference to one or more features that may be covered by one or more of the claims. Materials, processes and numerical examples described above are exemplary only, and should not be deemed to limit the claims.

Hardware, software and/or firmware can be used to implement the logic steps and/or processes of the invention (i.e., under the control of the processing unit 12). It should further be appreciated that such logic steps or process can be implemented as computer-executable instructions stored on a non-transitory computer readable medium, such a CD or DVD (including re-writable CDs and DVDs), flash or other non-volatile memory, ROM, EEPROM, disc drive, solid state drive, etc.

What is claimed is:

1. A notification device, comprising:
a housing;
a processing unit disposed in the housing, the processing unit including a clock and a processor;
a control panel on the housing and communicatively coupled to the processing unit;
a visual display on the housing and communicatively coupled to the processing unit;
the processing unit is configured to:
cause the display to visually display a dosage amount;
receive a first medication taken command from the control panel;
cause the display to visually display a time of day that the first medication taken command is received;
receive a second medication taken command from the control panel;
cause the display to visually replace the time of day that the first medication taken command is received with a time of day that the second medication taken command is received;
cause the display to visually display a number of times that medication taken commands are received from the control panel within a specified time period; and
cause the display to visually display a number of total medication taken within the specified time period, wherein the number of total medication taken is equal to the displayed dosage amount multiplied by the number of times that medication taken commands are received from the control panel within the specified time period.

2. The notification device of claim 1, wherein the specified time period is a preceding 24 hours.

3. The notification device of claim 1, wherein the processor is further configured to:
receive a change of dosage amount command from the control panel; and
cause the display to change the displayed dosage amount in response to the received change of dosage amount command.

4. The notification device of claim 1, further comprising:
one or more straps attached to the housing for securing the housing to a container holding medication.

5. The notification device of claim 1, wherein the processing unit further includes memory for storing historical time of day information relating to received medication taken commands.

6. The notification device of claim 5, wherein the processing unit is further configured to cause the display to visually display the historical time of day information in response to a command from the control panel.

7. The notification device of claim 5, further comprising:
a port communicatively coupled to the processing unit for communicating the stored time of day information relating to received medication taken commands.

8. The notification device of claim 7, wherein the port is a wireless network transceiver.

9. The notification device of claim 1, further comprising:
a locking arm extending from the housing and communicatively coupled to the processing unit, wherein the locking arm is movable between a locked position and an unlocked position;
wherein the processing unit is further configured to unlock the locking arm so that the locking arm can be moved from the locked position to the unlocked position only after a predetermined time period has expired since the last receipt of a medication taken command from the control panel and only if the displayed number of total medication taken within the specified time period is below a predetermined number.

10. The notification device of claim 9, wherein the processing unit is further configured to:
cause the display to visually display the predetermined time period;
receive a predetermined time period command from the control panel;
cause the display to visually change the displayed predetermined time period in response to the received predetermined time period command;
cause the display to visually display the predetermined number;
receive a predetermined number command from the control panel; and
cause the display to visually change the displayed predetermined number in response to the received predetermined number command.

11. The notification device of claim 1, further comprising:
a locking arm extending from the housing and communicatively coupled to the processing unit, wherein the locking arm is movable between a locked position and an unlocked position;
wherein the processing unit is further configured to unlock the locking arm so that the locking arm can be moved from the locked position to the unlocked position only after a predetermined time period has expired since the last receipt of a medication taken command from the control panel or only if the displayed number of total medication taken within the specified time period is below a predetermined number.

12. The notification device of claim 11, wherein the processing unit is further configured to:
cause the display to visually display the predetermined time period;
receive a predetermined time period command from the control panel;
cause the display to visually change the displayed predetermined time period in response to the received predetermined time period command;
cause the display to visually display the predetermined number;
receive a predetermined number command from the control panel; and
cause the display to visually change the displayed predetermined number in response to the received predetermined number command.

13. A notification device, comprising:
a housing;
a visual display on the housing including:
a dosage taken display,
a time of day display, and
a number of times used display;
a control panel on the housing operatively connected to the visual display, and including:
a first control button configured to increment the dosage taken display,
second control buttons configured to increment the time of day display, and
a third control button configured to increment the number of times used display.

14. The notification device of claim 13, wherein the time of day display comprises:
a day of the week display, and
a time of day display;
wherein the second control buttons comprise:
a first button configured to increment the day of the week display, and
a second button configured to increment the time of day display.

* * * * *